US008961477B2

(12) United States Patent
Wolter et al.

(10) Patent No.: US 8,961,477 B2
(45) Date of Patent: Feb. 24, 2015

(54) DELIVERY OF IMMUNE RESPONSE MODIFIER COMPOUNDS

(75) Inventors: James T. Wolter, Oakdale, MN (US); Ross M. Kedl, Denver, CO (US)

(73) Assignee: 3M Innovative Properties Company, St. Paul, MN (US)

( * ) Notice: Subject to any disclaimer, the term of this patent is extended or adjusted under 35 U.S.C. 154(b) by 1559 days.

(21) Appl. No.: 10/595,073

(22) PCT Filed: Aug. 25, 2004

(86) PCT No.: PCT/US2004/027633
§ 371 (c)(1),
(2), (4) Date: Jan. 30, 2006

(87) PCT Pub. No.: WO2005/020912
PCT Pub. Date: Mar. 10, 2005

(65) Prior Publication Data
US 2006/0195067 A1     Aug. 31, 2006

Related U.S. Application Data (60) Provisional application No. 60/497,628, filed on Aug. 25, 2003.

(51) Int. Cl.
*A61M 25/00* (2006.01)
*A61K 9/00* (2006.01)
*A61K 31/4745* (2006.01)
*A61M 37/00* (2006.01)

(52) U.S. Cl.
CPC ............ *A61K 9/0021* (2013.01); *A61K 31/4745* (2013.01); *A61M 37/0015* (2013.01); *A61M 2037/0046* (2013.01)
USPC ........................................................ 604/265

(58) Field of Classification Search
None
See application file for complete search history.

(56) References Cited

U.S. PATENT DOCUMENTS

| 2,893,392 A | 7/1959 | Wagner et al. |
| 3,034,507 A | 5/1962 | McConnell et al. |
| 3,072,122 A | 1/1963 | Rosenthal |
| 3,074,403 A | 1/1963 | Cooper et al. |
| 3,167,073 A | 1/1965 | Rosenthal |
| 3,221,740 A | 12/1965 | Rosenthal |
| 3,314,941 A | 4/1967 | Littell et al. |
| 3,678,150 A | 7/1972 | Szumski et al. |
| 3,964,482 A | 6/1976 | Gerstel et al. |
| 4,689,338 A | 8/1987 | Gerster |
| 4,698,348 A | 10/1987 | Gerster |
| 4,929,624 A | 5/1990 | Gerster et al. |
| 4,988,815 A | 1/1991 | Andre et al. |
| 5,037,986 A | 8/1991 | Gerster |
| 5,175,296 A | 12/1992 | Gerster |
| 5,238,944 A | 8/1993 | Wick et al. |
| 5,250,023 A | 10/1993 | Lee et al. |
| 5,266,575 A | 11/1993 | Gerster |
| 5,268,376 A | 12/1993 | Gester |
| 5,346,905 A | 9/1994 | Gerster |
| 5,352,784 A | 10/1994 | Nikolaides et al. |
| 5,367,076 A | 11/1994 | Gerster |
| 5,389,640 A | 2/1995 | Gerster et al. |
| 5,395,937 A | 3/1995 | Nikolaides et al. |
| 5,437,656 A | 8/1995 | Shikani et al. |
| 5,446,153 A | 8/1995 | Lindstrom et al. |
| 5,457,041 A | 10/1995 | Ginaven et al. |
| 5,482,936 A | 1/1996 | Lindstrom |
| 5,591,139 A | 1/1997 | Lin et al. |
| 5,611,806 A | 3/1997 | Jang |
| 5,679,647 A | 10/1997 | Carson et al. |
| 5,693,811 A | 12/1997 | Lindstrom |
| 5,697,901 A | 12/1997 | Eriksson |
| 5,741,908 A | 4/1998 | Gerster et al. |
| 5,756,747 A | 5/1998 | Gerster et al. |
| 5,804,566 A | 9/1998 | Carson et al. |
| 5,848,991 A | 12/1998 | Gross et al. |
| 5,853,383 A | 12/1998 | Murdock |
| 5,879,326 A | 3/1999 | Godshall et al. |
| 5,910,306 A | 6/1999 | Alving |
| 5,928,207 A | 7/1999 | Pisano et al. |
| 5,939,090 A | 8/1999 | Beaurline et al. |
| 5,980,898 A | 11/1999 | Glenn et al. |
| 5,983,136 A | 11/1999 | Kamen |
| 6,028,076 A | 2/2000 | Hirota et al. |
| 6,039,969 A | 3/2000 | Tomai et al. |
| 6,050,988 A | 4/2000 | Zuck |
| 6,069,149 A | 5/2000 | Nanba et al. |
| 6,083,505 A | 7/2000 | Miller et al. |
| 6,110,929 A * | 8/2000 | Gerster et al. ................. 514/293 |
| 6,132,755 A | 10/2000 | Eicher et al. |
| 6,194,425 B1 | 2/2001 | Gerster et al. |
| 6,200,592 B1 | 3/2001 | Tomai et al. |
| 6,207,646 B1 | 3/2001 | Krieg et al. |

(Continued)

FOREIGN PATENT DOCUMENTS

| EP | 0 394 026 | 10/1990 |
| EP | 1 104 764 | 6/2001 |

(Continued)

OTHER PUBLICATIONS

Mikszta, Nature Medicine, vol. 8, No. 4, Apr. 2002.*
Krieg, Trends in Immunology, vol. 23, No. 2, Feb. 2002.*
Babiuk, JContRel, 66, 2000.*
Tighe, European Journal of Immnology, 30, 2000.*
Daddona, "Recent Advances in Peptide, Protein and Macromolecule Drug Delivery", *Current Opinion in Drug Discovery and Development*, 2(2); pp. 168-171 (1999).
Kaushik et al. "Lack of Pain Associated with Microfabricated Microneedles", *Anesthesia Analg.*, 92, pp. 502-504 (2001).
Henry et al., "Microfabricated Microneedles: A Novel Approach to Transdermal Drug Delivery", *J. Pharm Sci.*, 87, 8, pp. 922-925 (1998).
McAllister et al., "Microfabricated Microneedles for Gene and Drug Delivery", *Annual Review of Biomedical Engineering*, 2, pp. 289-313 (2000).

(Continued)

*Primary Examiner* — Susan Tran
*Assistant Examiner* — William Craigo (57) ABSTRACT

Delivery of one or more immune response modifiers (IRMs) across a biological barrier by the use of a microneedle device.

19 Claims, 3 Drawing Sheets

(56) References Cited

U.S. PATENT DOCUMENTS

| | | |
|---|---|---|
| 6,239,116 B1 | 5/2001 | Krieg et al. |
| 6,245,776 B1 | 6/2001 | Skwierczynski et al. |
| 6,256,533 B1 | 7/2001 | Yuzhakov et al. |
| 6,312,612 B1 | 11/2001 | Sherman et al. |
| 6,322,808 B1 | 11/2001 | Trautman et al. |
| 6,329,381 B1 | 12/2001 | Kurimoto et al. |
| 6,331,266 B1 | 12/2001 | Powell et al. |
| 6,331,310 B1 | 12/2001 | Roser et al. |
| 6,331,539 B1 | 12/2001 | Crooks et al. |
| 6,334,856 B1 * | 1/2002 | Allen et al. ............... 604/191 |
| 6,339,068 B1 | 1/2002 | Krieg et al. |
| 6,352,722 B1 | 3/2002 | Blair |
| 6,376,501 B1 * | 4/2002 | Isobe et al. ............ 514/263.37 |
| 6,376,669 B1 | 4/2002 | Rice et al. |
| 6,379,324 B1 | 4/2002 | Garstein et al. |
| 6,387,938 B1 | 5/2002 | Mizuguchi et al. |
| 6,406,705 B1 | 6/2002 | Davis et al. |
| 6,426,334 B1 | 7/2002 | Agrawal et al. |
| 6,451,810 B1 | 9/2002 | Coleman et al. |
| 6,454,755 B1 | 9/2002 | Godshall |
| 6,476,000 B1 | 11/2002 | Agrawal |
| 6,503,231 B1 | 1/2003 | Prausnitz et al. |
| 6,511,463 B1 | 1/2003 | Wood et al. |
| 6,518,265 B1 | 2/2003 | Kato et al. |
| 6,525,064 B1 | 2/2003 | Dellaria et al. |
| 6,532,386 B2 | 3/2003 | Sun et al. |
| 6,533,949 B1 | 3/2003 | Yeshurun et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,551,622 B1 | 4/2003 | Jackson |
| 6,558,361 B1 | 5/2003 | Yeshurun |
| 6,558,951 B1 | 5/2003 | Tomai et al. |
| 6,573,273 B1 | 6/2003 | Crooks et al. |
| 6,591,124 B2 | 7/2003 | Sherman et al. |
| 6,595,947 B1 | 7/2003 | Mikszta et al. |
| 6,603,998 B1 | 8/2003 | King et al. |
| 6,656,147 B1 | 12/2003 | Gertsek et al. |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,696,465 B2 | 2/2004 | Dellaria et al. |
| 6,706,728 B2 | 3/2004 | Hedenstrom et al. |
| 6,713,291 B2 | 3/2004 | King et al. |
| 6,743,211 B1 | 6/2004 | Prausnitz et al. |
| 6,743,920 B2 | 6/2004 | Lindstrom et al. |
| 6,756,382 B2 | 6/2004 | Coleman et al. |
| 6,770,480 B1 | 8/2004 | Canham |
| 6,797,276 B1 | 9/2004 | Glenn et al. |
| 6,797,718 B2 | 9/2004 | Dellaria et al. |
| 6,818,650 B2 | 11/2004 | Griesgraber |
| 6,881,203 B2 | 4/2005 | Delmore et al. |
| 6,908,453 B2 | 6/2005 | Fleming et al. |
| 6,931,277 B1 | 8/2005 | Yuzhakov et al. |
| 7,387,271 B2 | 6/2008 | Noelle et al. |
| 2002/0016332 A1 | 2/2002 | Slade |
| 2002/0055517 A1 | 5/2002 | Smith |
| 2002/0058674 A1 | 5/2002 | Hedenstrom et al. |
| 2002/0082543 A1 | 6/2002 | Park et al. |
| 2002/0095134 A1 | 7/2002 | Pettis et al. |
| 2002/0102292 A1 | 8/2002 | Cormier et al. |
| 2002/0110840 A1 | 8/2002 | Tomai et al. |
| 2002/0128599 A1 | 9/2002 | Cormier et al. |
| 2002/0138049 A1 | 9/2002 | Allen et al. |
| 2002/0169416 A1 | 11/2002 | Gonnelli et al. |
| 2002/0177839 A1 | 11/2002 | Cormier et al. |
| 2002/0177858 A1 | 11/2002 | Sherman et al. |
| 2002/0193729 A1 * | 12/2002 | Cormier et al. ................. 604/46 |
| 2002/0198509 A1 | 12/2002 | Mikszta et al. |
| 2003/0093040 A1 | 5/2003 | Mikszta et al. |
| 2003/0130299 A1 | 7/2003 | Crooks et al. |
| 2003/0133913 A1 * | 7/2003 | Tomai et al. ................ 424/93.7 |
| 2003/0135161 A1 | 7/2003 | Fleming et al. |
| 2003/0135166 A1 | 7/2003 | Gonnelli |
| 2003/0135167 A1 | 7/2003 | Gonnelli |
| 2003/0135201 A1 | 7/2003 | Gonnelli |
| 2003/0139364 A1 * | 7/2003 | Krieg et al. ..................... 514/44 |
| 2003/0161797 A1 | 8/2003 | Miller et al. |
| 2003/0185835 A1 * | 10/2003 | Braun ........................ 424/184.1 |
| 2003/0199538 A1 | 10/2003 | Skwierczynski et al. |
| 2003/0207987 A1 | 11/2003 | Leong |
| 2004/0014779 A1 | 1/2004 | Gorden et al. |
| 2004/0049150 A1 | 3/2004 | Dalton et al. |
| 2004/0062813 A1 | 4/2004 | Cormier et al. |
| 2004/0091491 A1 * | 5/2004 | Kedl et al. .................. 424/178.1 |
| 2004/0096455 A1 | 5/2004 | Maa et al. |
| 2004/0115167 A1 | 6/2004 | Cormier et al. |
| 2004/0132079 A1 | 7/2004 | Gupta et al. |
| 2004/0141950 A1 * | 7/2004 | Noelle et al. ................ 424/85.1 |
| 2004/0147543 A1 | 7/2004 | Hays et al. |
| 2004/0162309 A1 * | 8/2004 | Gorden et al. ................ 514/292 |
| 2004/0171086 A1 | 9/2004 | Fink et al. |
| 2004/0175336 A1 | 9/2004 | Egging et al. |
| 2004/0176367 A1 | 9/2004 | Griesgraber et al. |
| 2004/0176732 A1 | 9/2004 | Frazier et al. |
| 2004/0180919 A1 | 9/2004 | Lee et al. |
| 2004/0181130 A1 | 9/2004 | Fox et al. |
| 2004/0181211 A1 | 9/2004 | Elliott et al. |
| 2004/0191833 A1 | 9/2004 | Fink et al. |
| 2004/0192585 A1 | 9/2004 | Fox et al. |
| 2004/0197865 A1 | 10/2004 | Gupta et al. |
| 2004/0202720 A1 | 10/2004 | Wightman et al. |
| 2004/0214851 A1 | 10/2004 | Birmachu et al. |
| 2004/0265354 A1 | 12/2004 | Ameri et al. |
| 2004/0265365 A1 | 12/2004 | Daddona et al. |
| 2005/0025778 A1 | 2/2005 | Cormier et al. |
| 2005/0049549 A1 | 3/2005 | Wong et al. |
| 2005/0054590 A1 | 3/2005 | Averett |
| 2005/0065463 A1 | 3/2005 | Tobinaga et al. |
| 2005/0090009 A1 | 4/2005 | Cormier et al. |
| 2005/0106226 A1 | 5/2005 | Cormier et al. |
| 2005/0106227 A1 | 5/2005 | Zalipsky et al. |
| 2005/0123565 A1 | 6/2005 | Subramony et al. |
| 2005/0235372 A1 | 10/2005 | Akira et al. |
| 2005/0261631 A1 | 11/2005 | Clarke et al. |

FOREIGN PATENT DOCUMENTS

| | | |
|---|---|---|
| JP | 9-208584 | 8/1997 |
| JP | 9-255926 | 3/1999 |
| JP | 11-222432 | 8/1999 |
| JP | 2000-247884 | 9/2000 |
| WO | WO 96/10630 | 4/1996 |
| WO | WO 00/35530 | 6/2000 |
| WO | WO 00/75304 | 12/2000 |
| WO | WO 0076519 A1 * | 12/2000 |
| WO | WO 01/36037 | 5/2001 |
| WO | WO 01/74343 | 10/2001 |
| WO | WO 02/07813 | 1/2002 |
| WO | WO 02/08595 | 1/2002 |
| WO | WO 02/24225 | 3/2002 |
| WO | WO0224225 A1 * | 3/2002 |
| WO | WO 02/36592 | 5/2002 |
| WO | WO 02/46194 | 6/2002 |
| WO | WO 02/46749 | 6/2002 |
| WO | WO 02/102377 | 12/2002 |
| WO | WO 03/020359 | 3/2003 |
| WO | WO 03/020889 | 3/2003 |
| WO | WO 03/043572 | 5/2003 |
| WO | WO 03/043573 | 5/2003 |
| WO | WO 03043572 A2 * | 5/2003 |
| WO | WO 03/045391 | 6/2003 |
| WO | WO 03/061636 | 7/2003 |
| WO | WO 03/097641 | 11/2003 |
| WO | WO 2004/091500 | 10/2004 |

(56) References Cited

FOREIGN PATENT DOCUMENTS

| WO | WO 2005016275 A2 * | 2/2005 |
|---|---|---|
| WO | WO 2005/020912 | 3/2005 |
| WO | WO 2005/051455 | 6/2005 |

OTHER PUBLICATIONS

McAllister et al., "Solid and Hollow Microneedles for Transdermal Protein Delivery", *Proceed. Int'l Symp. Control Release of Bioactive Material*, 26, CRS, pp. 192-193 (1999).
Geisse et al., *J. Am. Acad. Dermatol.*, 47(3): 390-398 (2002).
Shumack et al., *Arch. Dermatol.*, 138: 1163-1171 (2002).
Wozniak, et al, "The Amination of 3-nitro-1, 5-naphthyridines by Liquid Ammonia/Potassium Permanganate[1,2]. A New and Convenient Amination Mefthod.", *Journal of the Royal Netherlands Chemical Society*, 102, pp. 511-513, Dec. 12, 1983.
Brennan, et al, "Automated Bioassay of Interferons in Micro-test Plates", *Biotechniques*, June/July, 78, 1983.
Testerman, et al., "Cytokine Induction by the Immunomodulators Imiquimod and S-27609", *Journal of Leukocyte Biology*, vol. 58, pp. 365-372, Sep. 1995.
Bachman, et al, "Synthesis of Substituted Quinolylamines. Derivatives of 4-Amino-7-Chloroquinoline", *J. Org. Chem*, 15, pp. 1278-1284 (1950).
Jain, et al, "Chemical and Pharmacological Investigations of Some ω-Substituted Alkylamino-3-aminopyridines", *J. Med. Chem.*, 11, pp. 87-92 (1968).
Baranov, et al., *Chem. Abs.* 85, 94362, (1976).
Berényi, et al, "Ring Transformation of Condensed Dihydro-astriazines", *J. Heterocyclic Chem.*, 18, pp. 1537-1540 (1981).
Chollet, et al, "Development of a Topically Active Imiquimod Formulation", *Pharmaceutical Development and Technology*, 4(1), pp. 35-43 (1999).
Izumi, et al., "1$H$-Imidazo[4,5-$c$]quinoline Derivatives as Novel Potent TNF-α Suppressors: Synthesis and Structure-Activity Relationship of 1-, 2- and 4-Substituted 1$H$-imidazo[4,5-$c$]pyridines", *Bioorganic & Medicinal Chemistry*, 11, pp. 2541-2550 (2003).
Glenn et al., "Advance in Vaccine Delivery: Transcutaneous Immunisation", *Exp. Opin. Invest. Drugs*, 8(6), pp. 797-805 (1999).
IOMAI Datasheet, IOMAI Corporation, Retrieved from the internet on Jul. 22, 2003, 6 pages total.
Georgia Institute of Technology, "Taking the 'Ouch' Out of Needles: Arrays of 'Microneedles' Offer New technique for Drug Delivery", press release Jun. 23, 1998.
Pharmdata, "PharmData, Inc. Inks Contract With Vaccine Expert in Skin Immunizations", press release May 2, 2002.
Ito et al. 2002 (Roles of Toll-Like Receptors in Natural Interferon-Producing Cells as Sensors in Immune Surveillance, Human Immunology; 63:1120-1125).

* cited by examiner

DELIVERY OF IMMUNE RESPONSE MODIFIER COMPOUNDS

CROSS REFERENCE TO RELATED APPLICATIONS

This application claims priority from U.S. Provisional Application Ser. No. 60/497,628, filed Aug. 25, 2003 the entire contents of which is herein incorporated by reference.

BACKGROUND

There has been a major effort in recent years, with significant successes, to discover new drug compounds that act by stimulating certain key aspects of the immune system, as well as by suppressing certain other aspects (see, e.g., U.S. Pat. Nos. 6,039,969 and 6,200,592). These compounds, referred to herein as immune response modifiers (IRMs), appear to act through basic immune system mechanisms known as toll-like receptors to induce selected cytokine biosynthesis and may be used to treat a wide variety of diseases and conditions. For example, certain IRMs may be useful for treating viral diseases (e.g., human papilloma virus, hepatitis, herpes), neoplasias (e.g., basal cell carcinoma, squamous cell carcinoma, actinic keratosis, melanoma), and TH2-mediated diseases (e.g., asthma, allergic rhinitis, atopic dermatitis, multiple sclerosis), and are also useful as vaccine adjuvants. Many of the IRM compounds are small organic molecule imidazoquinoline amine derivatives (see, e.g., U.S. Pat. No. 4,689,338), but a number of other compound classes are known as well (see, e.g. U.S. Pat. No. 5,446,353; U.S. Pat. No. 6,194,425; and U.S. Pat. No. 6,110,929) and more are still being discovered. Other IRMs have higher molecular weights, such as oligonucleotides, including CpGs (see, e.g., U.S. Pat. No. 6,194,388). In view of the great therapeutic potential for IRMs, and despite the important work that has already been done, there is a substantial ongoing need for new means of controlling the delivery and activity of IRMs in order to expand their uses and therapeutic benefits.

SUMMARY

The usefulness of immune response modifiers (IRMs) in particular can be expanded and improved by delivering them across biological barriers with microneedle devices. Such delivery across biological barriers includes, for example, delivery of an IRM compound into or across the stratum corneum of the skin. This is particularly beneficial because the body's immune system cells upon which the IRMs act are highly available in this intracutaneous region. Moreover, while it permits enhanced activation of these cells, it can do so without requiring substantial systemic exposure. It is also useful for delivery directly into lesions that may otherwise have a thickened layer of keratinized skin reducing penetration of topical IRM formulations, such as can be the case with warts and various skin cancers.

Although published application US 2002/0193729 discloses in a laundry list two individual IRM compounds, imiquimod and resiquimod (4-Amino-α,α-dimethyl-1H-imidazo[4,5-c]quinoline-1-ethanol) for possible delivery in combination with a vaccine in a microneedle coating or reservoir, there are no examples using these compounds and apparently no recognition of the substantial benefits possible by delivering these and other IRMs using microneedles or that IRMs do not need to be coated or reservoired on the microneedles with a vaccine. Moreover, certain preferred IRMs and combinations described below—for example, non-TLR 7 agonists such as those that predominantly activate TRL 8 and/or 9 for certain uses, as well as those that activate CTL cell response—are certainly not recognized.

For example, IRM compounds that activate a strong cytotoxic lymphocyte (CTL) response may be particularly desirable as vaccine adjuvants, especially for therapeutic viral and/or cancer vaccines. IRM compounds that are TLR 8 agonists may be particularly desirable for use with therapeutic cancer vaccines. IRM compounds that are TLR 7 agonists and/or TLR 9 agonists may be particularly desirable for use with prophylactic vaccines. IRM compounds that are both TLR 7 and TLR 8 agonists may be particularly desirable for use with therapeutic viral vaccines and/or cancer vaccines. IRM compounds that are non-TLR 7 agonists, and do not induce substantial amounts of interferon-alpha, may be desirable for use with certain vaccines such as bacterial vaccines. IRM compounds that are conjugated to a vaccine antigen are particularly potent. IRM compounds given in combination with a tumor necrosis factor (TNF) receptor agonist, such as a CD40 agonist, are particularly potent, and may also be used in combination with a vaccine antigen. And all of these foregoing IRM compound types and combinations, although not required to be, can be beneficially delivered using a microneedle device to improve penetration into or across a biological barrier, such as the stratum corneum of the skin. IRM compounds that activate different TLRs and how to identify them are disclosed in, for example, pending applications WO 03/043573, U.S. 60/447179, U.S. 60/432650, U.S. 60/432651, and U.S. 60/450484, and IRM conjugates with vaccine antigens are disclosed is U.S. 60/403846, and IRM combinations with TNF receptor agonists are disclosed in U.S. 60/437398. Accordingly, the present invention provides IRM delivery devices that include a microneedle device and at least one IRM compound that is a TLR 6, 7, 8, and/or 9 agonist.

In some embodiments, the present invention provides an IRM delivery device adapted for delivery of an IRM compound that includes a microneedle device having at least one microneedle that penetrates a biological barrier by no more than 500 μm, and at least one IRM compound that is a TLR 6, 7, 8, and/or 9 agonist, with the proviso that when the IRM compound is located in a reservoir or coating on the microneedle device along with a vaccine the IRM compound is other than imiquimod or resiquimod. That is, a vaccine is not required to be associated with the device, but if it is used and it is in a reservoir or coating on the device, then the IRM compound can be any that is a TLR 6, 7, 8, and/or 9 agonist except for imiquimod and resiquimod.

In some embodiments, the present invention provides an IRM delivery device adapted for delivery of an IRM compound that includes a microneedle device having at least one microneedle that penetrates a biological barrier by no more than 500 μm, and at least one IRM compound that is a TLR 6, 7, 8, and/or 9 agonist, with the proviso that a vaccine is not in contact with the microneedle device prior to administration of the IRM compound.

Thus, vaccines may or may not be administered with the IRM. If a vaccine is used, it may or may not be in contact with the device. That is, it may or may not be in a reservoir or coating on the device. If a vaccine is in a reservoir or a coating on the device, the IRM compound is other than imiquimod or resiquimod.

In some embodiments, the present invention provides an IRM delivery device adapted for delivery of an IRM compound that includes a microneedle device having at least one microneedle that penetrates a biological barrier by no more than 500 μm, and at least one IRM compound that is a TLR 6, 8, and/or 9 agonist.

In some embodiments, the IRM delivery device may have a plurality of microneedles. This plurality of microneedles may be organized in an array.

In some embodiments of the IRM delivery device, at least one IRM compound may be coated onto at least a portion of the microneedle device.

In some embodiments, the microneedle device may include a reservoir in fluid communication with at least one microneedle. This reservoir may contain the at least one IRM compound. The IRM delivery apparatus of this embodiment may further include a pump or a microprocessor or both. A "pump" includes any non-diffusional mechanism for transporting the IRM and/or drug via the microneedles into or through the skin, such as, e.g., a mechanical pump or iontophoresis.

In some embodiments of the IRM delivery device, at least one microneedle may be hollow.

In some embodiments of the IRM delivery device, at least one microneedle may be solid.

In some embodiments of the IRM delivery device, at least one microneedle may be porous.

In some embodiments, the IRM delivery device may include more than one IRM compound. More than one IRM compound may be coated onto at least a portion of the microneedle device.

In some embodiments, the IRM delivery device may further include an additional drug. The at least one IRM compound and the additional drug may be coated onto at least a portion of the microneedle device. The additional drug may be a vaccine, including, for example, a DNA vaccine or a cell-based vaccine. The at least one IRM compound may be physically or chemically linked to the vaccine so as to form a unit. Both the at least one IRM compound and the vaccine may be coated onto at least a portion of the microneedle device. The additional drug may be a TNF receptor agonist, including, for example, a CD40 agonist. The additional drug may include both a vaccine and a TNF receptor agonist.

In another aspect, the present invention also provides a method for the delivery of an IRM compound into or across a biological barrier that includes: contacting a biological barrier with a microneedle device having at least one microneedle that penetrates the barrier by no more than 500 μm; and administering at least one IRM compound that is a TLR 6, 7, 8, and/or 9 agonist into or across the biological barrier; and optionally administering a vaccine; with the proviso that when the IRM compound is located in a reservoir or coating on the microneedle device along with the vaccine, the IRM compound is other than imiquimod or resiquimod.

In another aspect, the present invention provides a method for the delivery of an IRM compound into or across a biological barrier that includes: contacting a biological barrier with a microneedle device having at least one microneedle that penetrates the barrier by no more than 500 μm; administering at least one IRM compound that is a TLR 6, 7, 8, and/or 9 agonist into or across the biological barrier; and optionally administering a vaccine; with the proviso that the vaccine is not in contact with the microneedle device prior to administration of the IRM compound.

In still another aspect, the present invention provides a method for the delivery of an IRM compound into or across a biological barrier that includes: contacting a biological barrier with a microneedle device having at least one microneedle that penetrates the barrier by no more than 500 μm; and administering at least one IRM compound that is a TLR 6, 8, and/or 9 agonist into or across the biological barrier. In a preferred embodiment of the method, the biological barrier may be the skin and the at least one IRM compound may be delivered intracutaneously.

In some embodiments of the method, the contacting of the skin with a microneedle device occurs prior to contacting the skin with at least one IRM compound. This contacting of the skin with at least one IRM compound may be by applying the at least one IRM compound topically to the skin. The at least one IRM compound may be contained in a solution, ointment, gel, foam, or emulsion.

In some embodiments of the method, the contacting of the skin with at least one IRM compound occurs prior to the contacting the skin with a microneedle device. This contacting of the skin with at least one IRM compound may be by applying the at least one IRM compound topically to the skin. The at least one IRM compound may be contained in a solution, ointment, gel, foam, or emulsion.

Examples of IRM compound that may be applied topically before or after the microneedles include but are not limited imiquimod cream (e.g., Aldara™) and resiquimod gel formulation.

In some embodiments of the method, the contacting of the skin with a microneedle device may occur coincident with contacting the skin with at least one IRM compound; the at least one IRM compound may be coated on at least a portion of the microneedle device. Some embodiments of the method further include the intracutaneous administration of a vaccine.

In another aspect, the present invention also provides a method of treating a lesion on the skin or mucosa with the application of a microneedle device to the lesion in conjunction with the application of at least one IRM compound. In some embodiments, the lesion may be a neoplastic condition, associated with melanoma, associated with basal cell carcinoma, actinic keratosis, or squamous cell carcinoma, or the lesion may be associated with a viral infection, including, for example, a wart.

In another aspect, the present invention also provides kits including a microneedle device and one or more immune response modifier (IRM) compounds.

In some embodiments of the present invention, at least one IRM compound may be an agonist of at least one TLR, preferably an agonist of TLR6, TLR7, or TLR8. The IRM may also in some cases be an agonist of TLR 9. In some embodiments of the present invention, at least one IRM compound may be a small molecule immune response modifier (e.g., molecular weight of less than about 1000 daltons). In other embodiments of the present invention, at least one IRM compound may be a CpG compound or derivative thereof.

In some embodiments of the present invention, at least one IRM compound may include a 2-aminopyridine fused to a five-membered nitrogen-containing heterocyclic ring, or a 4-aminopyrimidine fused to a five-membered nitrogen-containing heterocyclic ring.

In some embodiments of the present invention, at least one IRM compound may be an imidazoquinoline amine including, but not limited to, amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, and thioether substituted imidazoquinoline amines; a tetrahydroimidazoquinoline amine including, but not limited to, amide substituted tetrahydroimidazoquinoline amines, sulfonamide substituted tetrahydroimidazoquinoline amines, urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, and thioether substituted tetrahydroimidazoquinoline amines; an imidazopyridine amine including, but not limited to, amide substituted imidazopyridines, sulfonamido substituted imidazopyridines, and urea substituted imidazopyridines; 1,2-bridged imidazoquinoline amines; 6,7-fused cycloalkylimidazopyridine amines; imidazonaphthyridine amines; tetrahydroimidazonaphthyridine amines; oxazoloquinoline amines; thiazoloquinoline amines; oxazolopyridine amines; thiazolopyridine amines; oxazolonaphthyridine amines; thiazolonaphthyridine amines; pharmaceutically acceptable salts thereof; and combinations thereof.

In some embodiments, at least one IRM compound may be a purine, imidazoquinoline amide, benzimidazole, 1H-imidazopyridine, adenine, or a derivative thereof.

The term "comprises" and variations thereof do not have a limiting meaning where these terms appear in the description and claims, As used herein, "a," "an," "the," "at least one," and "one or more" are used interchangeably.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. Various other features and advantages of the present invention should become readily apparent with reference to the following detailed description, examples, claims and appended drawings. In several places throughout the specification, guidance is provided through lists of examples. In each instance, the recited list serves only as a representative group and should not be interpreted as an exclusive list.

DETAILED DESCRIPTION OF ILLUSTRATIVE EMBODIMENTS OF THE INVENTION

Figure 1:
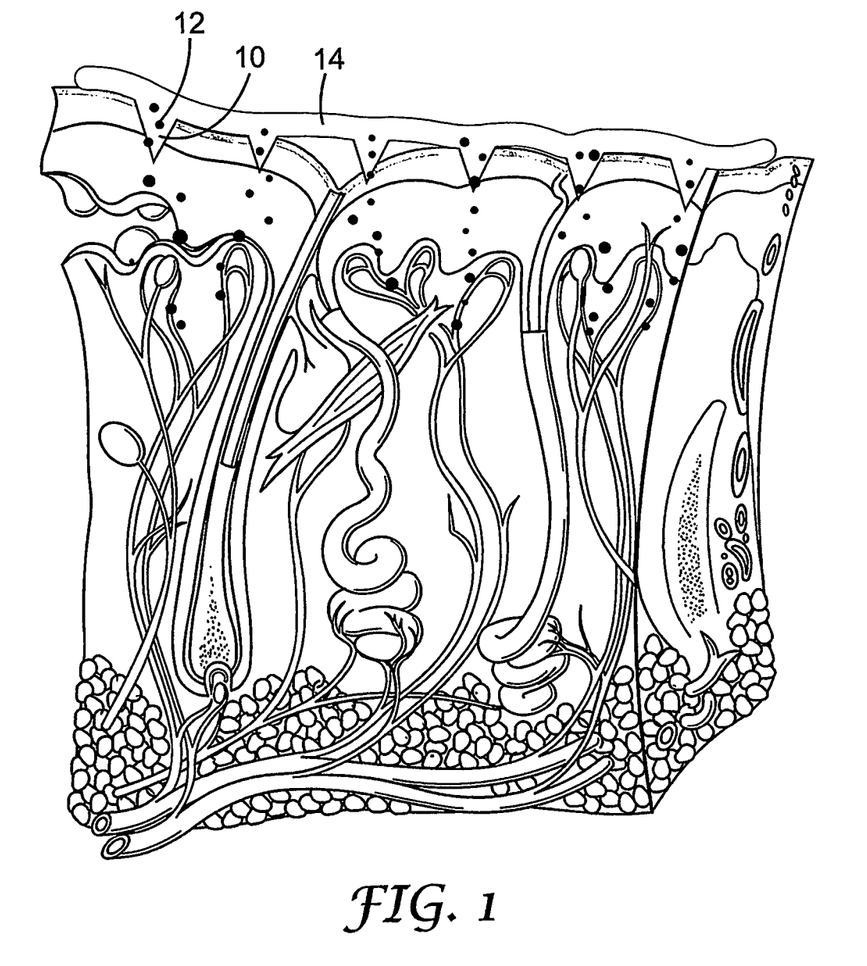
FIG. 1 shows a diagrammatic cross-section of skin after having been penetrated with a microneedle device and an IRM compound subsequently applied.
Figure 2:
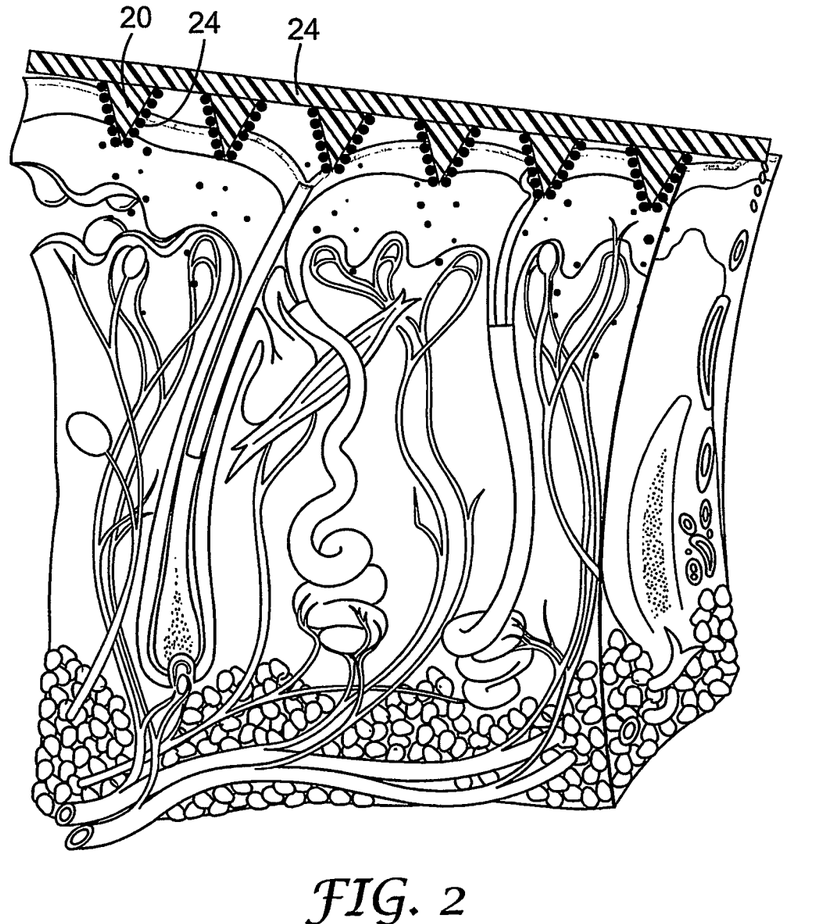
FIG. 2 shows a diagrammatic cross-section of skin penetrated with a microneedle device and an IRM compound coated onto the needles.
Figure 3:
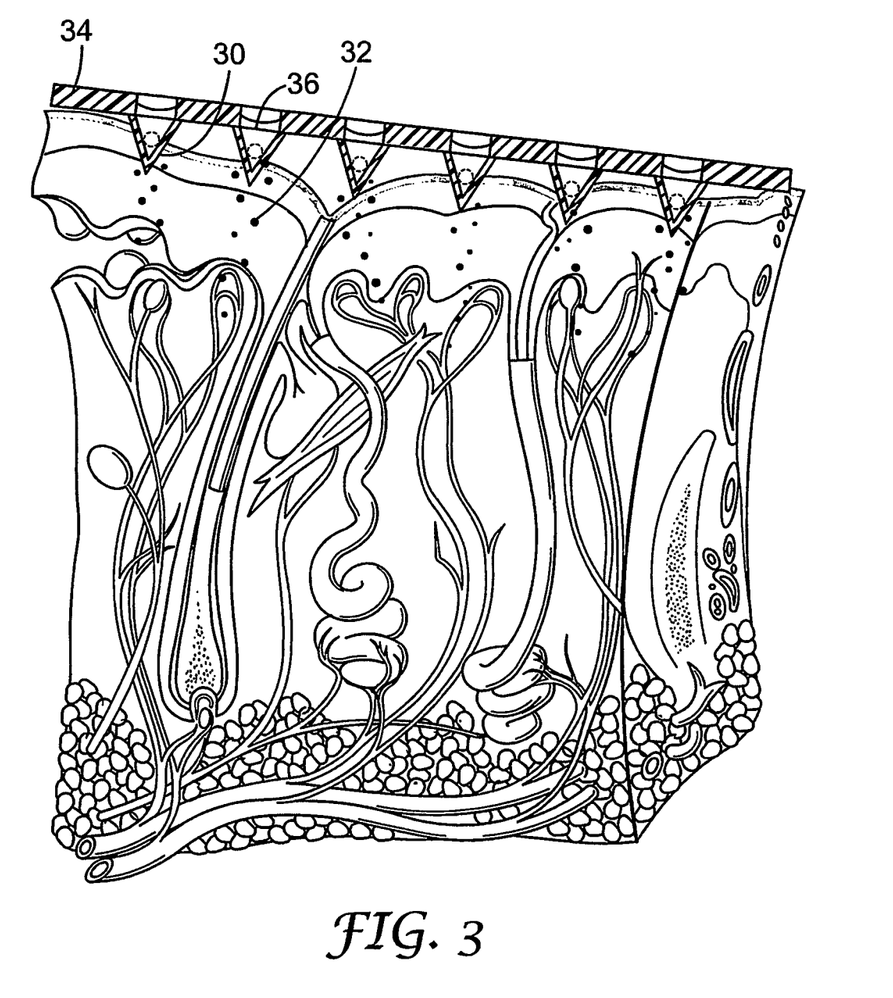
FIG. 3 shows a diagrammatic cross-section of skin penetrated with a microneedle device and an IRM compound being delivered via channels from a reservoir.

The present invention provides an IRM delivery device to be used for the delivery of cytokine inducing and/or suppressing immune response modifier (IRM) compounds across a variety of biological barriers. In a preferred embodiment, as shown in FIGS. 1-3, the IRM delivery device of the present invention may be used to affect the delivery of an IRM compound across the stratum corneum (the outermost layer of the skin) into the intracutaneous space. If desired, the IRM can also be delivered transdermally through the skin for systemic administration.

The present invention also provides methods for the delivery of IRM compounds, alone or in combination with a variety of other agents, across a biological barrier through the use of a microneedle device. The microneedle device effectively pierces the biological barrier such that DIM compounds, alone or in combination with other agents, can pass through the biological barrier into the tissues below. The microneedle device may be used at the site of interest before or after applying one or more IRM compounds to the site of interest. Alternatively, the microneedle device may be used at the site of interest coincident with contacting the site of interest with one or more IRM compounds.

Biological barriers can include, but are not limited to, the skin (or parts thereof), mucosal tissue (including, for example, oral, nasal, ocular, vaginal, urethral, gastrointestinal, and respiratory surfaces), the blood-brain barrier, periodontal surfaces, blood vessels, lymphatic vessels, or cell membranes. A target biological barrier may be located within normal, intact tissue. A target biological barrier may be located within damaged or diseased tissue, such as a wound or lesion. When internal delivery to a biological barrier is desired, surgical access to the desired delivery site may be provided. Access to an internal site may also be provided through laproscopic instruments and/or catheters.

A preferred embodiment of the present invention provides methods for the intracutaneous delivery of one or more IRM compounds, alone or in combination with a variety of other agents, across the stratum corneum. In the methods of the present invention, microneedle devices and IRM delivery devices are used to pierce a biological barrier. Typically, a microneedle device or IRM delivery device is pressed against the stratum corneum, effectively piercing the stratum corneum, such that IRM compounds, alone or in combination with other agents, can pass through the stratum corneum into the tissues below. The length of the microneedles can be adjusted to achieve a desired penetration depth.

While the microneedle devices and IRM delivery device disclosed herein can be applied to any biological barrier, they are typically applied to skin. Mammalian skin contains two layers, the epidermis and dermis. The epidermis is made up of five layers, the stratum corneum, the stratum lucidum, the stratum granulosum, the stratum spinosum and the stratum germinativum. The dermis is made up of two layers, the upper papillary dermis and the deeper reticular dermis. The stratum corneum is the outer layer, and is generally between 10 and 50 cells, or between 10 and 20 micrometers thick. Unlike other tissue in the body, the stratum corneum contains cells (called keratinocytes) filled with bundles of cross-linked keratin and keratohyalin surrounded by an extracellular matrix of lipids. It is this structure that gives skin its barrier properties and which prevents therapeutic intracutaneous or transdermal administration of many drugs. Below the stratum corneum are the other four layers of epidermis, which together typically are between 50 and 100 micrometers thick. The viable epidermis contains no blood vessels. Beneath the epidermis is the dermis, which is between 1 millimeters and 3 millimeters thick and contains blood vessels, lymphatics, and nerves. The thickness of the dermis and epidermis varies from individual to individual, and within an individual, at different locations on the body. For example, it has been reported that in humans the epidermis varies in thickness from about 40 micrometers to about 90 micrometers and the dermis varies in thickness ranging from just below the epidermis to a depth of from less than 1 millimeters in some regions of the body to just under 2 millimeters to about 4 millimeter in other regions of the body.

As used herein, "intracutaneous" is intended to mean administration of an agent into or across the stratum corneum into the skin. Intracutaneous delivery can include delivery into the epidermis (also referred to as intraepidermal delivery) or dermis (also referred to as intradermal delivery). An example of such intracutaneous delivery is shown in FIG. 1, where the skin has been penetrated by microneedles (not shown) that have been removed leaving microperforations 10 through which IRM compound 12 is delivered via a topical preparation 14. An agent delivered intracutaneously may, depending on the physical and chemical nature of the agent, remain near the delivery site for an extended period or be rapidly absorbed into the blood capillaries and/or lymphatic vessels to become systemically bioavailable. An agent delivered intracutaneously may also be taken up directly by cells located within the skin, including, for example, antigen presenting cells (APC), such as epidermal Langerhan's cells and dermal dendritic cells. As used herein, "transdermal" is intended to mean the administration of an agent across the skin for systemic delivery.

As used herein, a "microneedle device" includes at least one, but usually a plurality of microneedles attached to or protruding from the surface of a substrate. While it is possible a microneedle device could have only one or two microneedles, a microneedle device will typically have more than two microneedles, and will usually have many tens, hundreds, or thousands of needles. The microneedles may be arranged in any desired pattern over the surface of the substrate. For example, the microneedles may be arranged in an array pattern or the microneedles may be distributed randomly over the surface of the substrate. As used herein the "substrate" of a microneedle device includes the base to which the microneedles are attached or integrally formed. Such substrates can be constructed from a variety of materials, including, for example, metals, ceramics, semiconductors, organics, polymers, and composites. The substrate and/or microneedles, as well as other components, may be formed from flexible materials to allow the device to fit the contours of the biological barrier.

As used herein, the term "microneedle" refers to any needle-like structure having a height above the substrate surface from which they protrude of about 500 micrometers or less. In some instances, the height of the microneedle may be about 250 micrometers, about 100 micrometers, or less. When the a microneedle of the present invention is used for the intracutaneous delivery of an IRM compound, the height of the microneedle is preferably sufficient to pass through the stratum corneum and into the dermis. It is also, however, preferable that the height of the microneedles is not sufficiently large to stimulate nerves in deeper tissue and cause pain when inserted at a delivery site. Such use of microneedles for the intracutaneous delivery of IRM compounds has many advantages. For example, the delivery of IRM compounds can be accomplished without pain and without bleeding. Thus the methods and IRM delivery apparatus of the present invention allow for the delivery of an IRM compound to a subject in a minimally invasive manner. With the delivery of IRM compounds, one is no longer relying on diffusion to transport the IRM compound through the stratum corneum. Thus, the amount of IRM compound to be administered may be reduced and IRM compounds administered intracutaneously can be absorbed more rapidly.

The selection of the microneedles to serve for the delivery of an IRM compound can vary widely within the scope of the invention. Microneedles may be manufactured from a variety of materials. Material selection may be based on a variety of factors including, for example, the ability of the material to accurately reproduce a desired pattern, the strength and toughness of the material when formed into the microneedles, the compatibility of the material with, for example, human or animal skin, and the compatibility of the materials with any fluids that will be expected to contact the microneedle devices. Microneedles may be constructed from, for example, glassy materials, metals, ceramics, semiconductors, organics, polymers, including biodegradable polymers, composites, and combinations of such materials. Preferred materials of construction can include pharmaceutical grade stainless steel, gold, titanium, nickel, iron, gold, tin, chromium, copper, alloys of these or other metals, silicon, silicon dioxide, and polymers. Representative biodegradable polymers include polymers of hydroxy acids such as lactic acid and glycolic acid polylactide, polyglycolide, polylactide-co-glycolide, and copolymers with PEG, polyanhydrides, poly(ortho)esters, polyurethanes, poly(butyric acid), poly(valeric acid), and poly(lactide-co-caprolactone). Representative non-biodegradable polymers include polycarbonate, polymethacrylic acid, ethylenevinyl acetate, polytetrafluorethylene (TEFLON), and polyesters. Among polymeric materials it may be preferred that the microneedles be manufactured of thermoplastice materials. Such suitable polymeric materials for the microneedles of the present invention may include, but are not limited to: acrylonitrile-butadiene-styrenes, polyphenyl sulfides, polycarbonates, polypropylenes, acetals, acrylics, polyetherimides, polybutylene terephthalates, polyethylene terephthalates, etc. Polymeric microneedles may be manufactured from a single polymer or a mixture/blend of two or more polymers.

Generally, microneedles should have the mechanical strength to remain intact while being inserted into the skin and while being removed from the skin. Also, in some embodiments, it may be desirable to leave the microneedle device attached to the skin to provide continuous delivery of an MM compound. For such continuous delivery, it is desired that the microneedles remain intact while remaining in place for up to a number of days. Another approach is for some or all of the microneedle to detach and remain in the skin, for example if a biodegradable material is used.

The microneedle structure of the microneedle devices of the present invention can be porous, solid, or hollow. As used herein, the term "porous" means having pores or voids throughout at least a portion of the microneedle structure, sufficiently large and sufficiently interconnected to permit passage of fluid and/or solid materials through the microneedle. As used herein, the term "hollow" means having one or more substantially annular bores or channels through the interior of the microneedle structure, having a diameter sufficiently large to permit passage of fluid and/or solid materials through the microneedle. The annular bores may extend throughout all or a portion of the needle in the direction of the tip to the base, extending parallel to the direction of the needle or branching or exiting at a side of the needle, as appropriate. A solid or porous microneedle can be hollow. One of skill in the art can select the appropriate porosity and/or bore features required for specific applications.

In some microneedle devices, the movement of a fluid toward or away from the microneedles may be accomplished by a capillary wicking action. In such instances, coatings may be provided, for example, hydrophilic coatings, that enhance the capillary wicking action.

The microneedles may have straight or, as shown in FIGS. 2-3, tapered shafts 20 and 30, respectively. Microneedles may be formed with shafts that have a circular cross-section in the perpendicular, or the cross-section can be non-circular. The cross-sectional dimensions may be between 10 nanometers and 1 millimeter, preferably between 1 micrometer and 200 micrometers, and more preferably between 10 micrometers and 100 micrometers. Microneedles can be oriented perpendicular or at an angle to the substrate.

FIG. 2 shows an arrangement where the microneedles 20 extend from a substrate 24 and are coated with IRM compound 22 being delivered.

As shown in FIG. 3, a microneedle device may include a fluid reservoir 36 in communication with the microneedles 30 attached to a substrate 34 for delivery an IRM compound 32 intradermally. If hollow microneedles are used, as shown, the hollow center may be in fluid communication with the fluid reservoir. The fluid reservoir may contain one or more IRM compounds and/or other agents, including for example a vaccine or another drug. A microneedle device may also include a pump and/or microprocessor (not shown).

For the delivery of more than one IRM compound, the IRM compounds may be contained within the fluid reservoir, the IRM compounds may be coated onto the microneedle device, or, a combination thereof may be used, in which one or more IRM compounds are contained within a reservoir and one or more IRM compounds are coated onto the microneedle device. When more that one IRM compound is delivered, the same or different concentrations and timings of delivery may be used for the various IRM compounds.

Microneedle devices of the present invention may be sterilizable using standard methods. Microneedle devices may be designed for a single-use, with the device being disposed of after initial use. Alternatively, the devices of the present invention may be designed for repeated use.

Examples of microneedle devices are disclosed in, for example, U.S. Pat. Nos. 2,893,392, 3,034,507, 3,167,073, 3,072,122, 3,964,482; 5,250,023; 5,591,139; 5,848,991; 5,879,326; 5,928,207; 6,256,533; 6,312,612; 6,331,266; 6,334,856; 6,379,324; 6,471,903; 6,503,231; 6,511,463; 6,533,949; 6,558,361; U.S. Patent Publication No. 2002/0128599; U.S. Patent Publication No. 2002/0193729; U.S. Patent Publication No. 2003/0045837; U.S. Patent Publication No. 2003/0135161; U.S. Provisional Application No. 60/424,774; WO 00/35530; and WO 03/20359.

The IRM microneedle delivery devices of the present invention include a microneedle device and at least one IRM compound. It should be understood that the microneedle devices of the IRM delivery devices of the present invention include, not only any of the microneedle devices described herein, but also any additional microneedle devices known or that become known, and are not necessarily limited to use of the particular microneedle devices disclosed herein.

Immune response modifiers ("IRM") useful in the present invention include compounds that act on the immune system by inducing and/or suppressing cytokine biosynthesis. IRM compounds possess potent immunostimulating activity including, but not limited to, antiviral and antitumor activity, and can also down-regulate other aspects of the immune response, for example shifting the immune response away from a TH-2 immune response, which is useful for treating a wide range of TH-2 mediated diseases. IRM compounds can also be used to modulate humoral immunity by stimulating antibody production by B cells. Further, various IRM compounds have been shown to be useful as vaccine adjuvants (see, e.g., U.S. Pat. No. 6,083,505, U.S. Pat. No. 6,406,705, and WO 02/24225).

In particular, certain IRM compounds effect their immunostimulatory activity by inducing the production and secretion of cytokines such as, e.g., Type I interferons, TNF-α, IL-1, IL-6, IL-8, IL-10, IL-12, MIP-1, and/or MCP-1, and can also inhibit production and secretion of certain TH-2 cytokines, such as IL-4 and IL-5. Some IRM compounds are said to suppress IL-1 and TNF (U.S. Pat. No. 6,518,265).

For some embodiments, the preferred IRM compounds are so-called small molecule IRMs, which are relatively small organic compounds (e.g., molecular weight under about 1000 daltons, preferably under about 500 daltons, as opposed to large biologic protein, peptides, and the like). Although not bound by any single theory of activity, some IRMs are known to be agonists of at least one Toll-like receptor (TLR). IRM compounds that are agonists for TLRs selected from 6, 7, 8, and/or 9 may be particularly useful for certain applications. In some applications, for example, when an IRM compound is administered in association with a vaccine coated on or in a reservoir of a microneedle device, the preferred IRM compound is not a TLR7 agonist and is a TLR 8 or TLR 9 agonist. Some small molecule IRM compounds are agonists of TLRs such as 6, 7, and/or 8, while oligonucleotide IRM compounds are agonists of TLR9, and perhaps others. Thus, in some embodiments, the IRM that is included in the IRM delivery apparatus may be a compound identified as an agonist of one or more TLRs.

For example, without being bound to any particular theory or mechanism of action, IRM compounds that activate a strong cytotoxic lymphocyte (CTL) response may be particularly desirable as vaccine adjuvants, especially for therapeutic viral and/or cancer vaccines because a therapeutic effect in these settings is dependent on the activation of cellular immunity. For example, studies have shown that activation of T cell immunity in a given patient has a significant positive effect on the prognosis of the patient. Therefore the ability to enhance T cell immunity is believed to be critical to producing a therapeutic effect in these disease settings.

IRM compounds that are TLR 8 agonists may be particularly desirable for use with therapeutic cancer vaccines because antigen presenting cells that express TLR8 have been shown to produce IL-12 upon stimulation through TLR8. IL-12 is believed to play a significant role in activation of CTLs, which are important for mediating therapeutic efficacy as described above.

IRM compounds that are TLR 7 agonists and/or TLR 9 agonists may be particularly desirable for use with prophylactic vaccines because the type I interferon induced by stimulation through these TLRs is believed to contribute to the formation of neutralizing Th1-like humoral and cellular responses.

IRM compounds that are both TLR 7 and TLR 8 agonists may be particularly desirable for use with therapeutic viral vaccines and/or cancer vaccines because TLR7 stimulation is believed to induce the production of type I IFN and activation of innate cells such as macrophages and NK cells, and TLR8 stimulation is believed to activate antigen presenting cells to initiate cellular adaptive immunity as described above. These cell types are able to mediate viral clearance and/or therapeutic growth inhibitory effects against neoplasms.

IRM compounds that are non-TLR 7 agonists, and do not induce substantial amounts of interferon alpha, may be desirable for use with certain vaccines such as bacterial vaccines because TLR7 induces type I IFN production, which down-regulates the production of IL-12 from macrophages and DCs. IL-12 contributes to the subsequent activation of macrophages, NK cells and CTLs, all of which contribute to anti-bacterial immunity. Therefore the induction of anti-bacterial immunity against some kinds of bacteria may be enhanced in the absence of IFNa.

For purposes of the present application, one way to determine if an IRM compound is considered to be an agonist for a particular TLR is if it activates an NFkB/luciferase reporter construct through that TLR from the target species more than about 1.5 fold, and usually at least about 2 fold, in TLR transfected host cells such as, e.g., HEK293 or Namalwa cells relative to control transfectants. For information regarding TLR activation, see, e.g., applications WO 03/043573, U.S. 60/447179, U.S. 60/432650, U.S. 60/432651, and U.S. 60/450484, WO 03/043588 and the other IRM patents and applications disclosed herein (hereby incorporated by reference).

Preferred IRM compounds include a 2-aminopyridine fused to a five-membered nitrogen-containing heterocyclic ring.

Examples of classes of small molecule IRM compounds include, but are not limited to, derivatives of imidazoquinoline amines including but not limited to amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamide ether substituted imidazoquinoline amines, urea substituted imidazoquinoline ethers, and thioether substituted imidazoquinoline amines; tetrahydroimidazoquinoline amines including but not limited to amide substituted tetrahydroimidazoquinoline amines, sulfonamide substituted tetrahydroimidazoquinoline amines, urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, and thioether substituted tetrahydroimidazoquinoline amines; imidazopyridine amines including but not limited to amide substituted imidazopyridines, sulfonamido substituted imidazopyridines, and urea substituted imidazopyridines; 1,2-bridged imidazoquinoline amines; 6,7-fused cycloalkylimidazopyridine amines; imidazonaphthyridine amines; tetrahydroimidazonaphthyridine amines; oxazoloquinoline amines; thiazoloquinoline amines; oxazolopyridine amines; thiazolopyridine amines; oxazolonaphthyridine amines; and thiazolonaphthyridine amines, such as those disclosed in, for example, U.S. Pat. Nos. 4,689,338; 4,929,624; 4,988,815; 5,037,986; 5,175,296; 5,238,944; 5,266,575; 5,268,376; 5,346,905; 5,352,784; 5,367,076; 5,389,640; 5,395,937; 5,446,153; 5,482,936; 5,693,811; 5,741,908; 5,756,747; 5,939,090; 6,039,969; 6,083,505; 6,110,929; 6,194,425; 6,245,776; 6,331,339; 6,376,669; 6,451,810; 6,525,064; 6,545,016; 6,545,017; 6,558,951; and 6,573,273; European Patent 0 394 026; U.S. Patent Publication No. 2002/0055517; and International Patent Publication No WO 01/74343; WO 02/46188; WO 02/46189; WO 02/46190; WO 02/46191; WO 02/46192; WO 02/46193; WO 02/46749; WO 02/102377; WO 03/020889; WO 03/043572 and WO 03/045391.

Additional examples of small molecule IRMs said to induce interferon (among other things), include purine derivatives (such as those described in U.S. Pat. Nos. 6,376, 501, and 6,028,076), imidazoquinoline amide derivatives (such as those described in U.S. Pat. No. 6,069,149), and benzimidazole derivatives (such as those described in U.S. Pat. No. 6,387,938). 1H-imidazopyridine derivatives (such as those described in U.S. Pat. No. 6,518,265) are said to inhibit TNF and IL-1 cytokines.

Examples of small molecule IRMs that include a 4-aminopyrimidine fused to a five-membered nitrogen-containing heterocyclic ring include adenine derivatives (such as those described in U.S. Pat. Nos. 6,376,501; 6,028,076 and 6,329, 381; and in WO 02/08595).

In some applications, for example, when an IRM compound is administered in association with a vaccine as a coating on or from a reservoir in a microneedle device, the preferred IRM compound is other than imiquimod or S-28463 (i.e., resiquimod: 4-Amino-α,α-dimethyl-1H-imidazo[4,5-c]quinoline-1-ethanol).

Examples of particular IRM compounds include 2-propyl [1,3]thiazolo[4,5-c]quinolin-4-amine, which is considered predominantly a TLR 8 agonist (and not a substantial TLR 7 agonist), 4-amino-α,α-dimethyl-1H-imidazo[4,5-c]quinoline-1-ethanol, which is considered predominantly a TLR 7 agonist (and not a substantial TLR 8 agonist), and 4-amino-2-(ethoxymethyl)-α,α-dimethyl-6,7,8,9-tetrahydro-1H-imidazo[4,5-c]quinoline-1-ethanol, which is a TLR 7 and TLR 8 agonist. In addition to its TLR 7 activity (and TLR 6 activity, but low TLR 8 activity), 4-amino-α,α-dimethyl-1H-imidazo [4,5-c]quinoline-1-ethanol has beneficial characteristics, including that it has a much lower CNS effect when delivered systemically compared to imiquimod. Other examples of specific IRM compounds include, e.g., N-[4-(4-Amino-2-butyl-1H-imidazo[4,5-c][1,5]naphthyridin-1-yl)butyl]-N'-cyclohexylurea, 2-Methyl-1-(2-methylpropyl)-1H-imidazo[4,5-c] [1,5]naphthyridin-4-amine, 1-(2-Methylpropyl)-1H-imidazo [4,5-c][1,5]naphthyridin-4-amine, N-{2-[4-amino-2-(ethoxymethyl)-1H-imidazo[4,5-c]quinolin-1-yl]-1,1-dimethylethyl}methanesulfonamide N-[4-(4-amino-2-ethyl-1H-imidazo[4,5-c]quinolin-1-yl)butyl]methanesulfonamide, 2-methyl-1-[5-(methylsulfonyl) pentyl]-1H-imidazo[4,5-c]quinolin-4-amine, N-[4-(4-amino-2-propyl-1H-imidazo[4,5-c]quinolin-1-yl)butyl] methanesulfonamide, 2-butyl-1-[3-(methylsulfonyl)propyl]-1H-imidazo[4,5-c]quinoline-4-amine, 2-butyl-1-{2-[(1-methylethyl)sulfonyl]ethyl}-1H-imidazo[4,5-c]quinolin-4-amine, N-{2-[4-amino-2-(ethoxymethyl)-1H-imidazo[4,5-c] quinolin-1-yl]-1,1-dimethylethyl}-N'-cyclohexylurea, N-{2-[4-amino-2-(ethoxymethyl)-1H-imidazo[4,5-c]quinolin-1-yl]-1,1-dimethylethyl}cyclohexanecarboxamide, N-{2-[4-amino-2-(ethoxymethyl)-1H-imidazo[4,5-c]quinolin-1-yl] ethyl}-N'-isopropylurea. Resiquimod, 4-amino-2-ethoxymethyl-α,α-dimethyl-1H-imidazo[4,5-c]quinoline-1-ethanol, may also be used in certain situations where a combination TLR 7 and TLR 8 agonist is desired, for example in application of the microneedle device into a viral or neoplastic lesion, or in combination with particular therapeutic viral or cancer vaccines, or delivered via a topical preparation to a site before or after application of the microneedle device.

Other M compounds include large biological molecules such as oligonucleotide sequences, Some IRM oligonucleotide sequences contain cytosine-guanine dinucleotides (CpG) and are described, for example, in U.S. Pat. Nos. 6,194,338; 6,207,646; 6,239,116; 6,339,068; and 6,406,705. Some CpG-containing oligonucleotides can include synthetic immunomodulatory structural motifs such as those described, for example, in U.S. Pat. Nos. 6,426,334 and 6,476,000. Other IRM nucleotide sequences lack CpG and are described, for example, in International Patent Publication No. WO 00/75304.

With the devices and methods of the present invention, one or more IRM compounds as described herein may be delivered across a biological barrier. Such IRM compounds may be in any pharmaceutically acceptable form, as will be familiar to those of skill in the art.

The microneedle device may release the IRM compound immediately or, in some embodiments, a microneedle device may be left in place for an extended period (e.g., beyond 30 seconds, usually 5 to 20 minutes or more) for delivery of the IRM compound, with the IRM compound moving through or around the microneedles to pass through the pierced sites into the target tissue. For example, one or more IRM compounds may be coated onto at least a portion of the microneedles, or one or more IRM compounds may be contained in a fluid reservoir component of a microneedle device, in either case there may also be included one or more other drugs, including vaccines, e.g., as a co-coating or in a reservoir. In some embodiments, when one or more vaccines is to be delivered along with one or more IRM compounds, the vaccine need not be associated with or in contact with the IRM delivery device, e.g., the one or more vaccines is not co-coated onto the IRM delivery device or is not contained in a fluid reservoir.

In some embodiments, a microneedle device may be removed from a target site, such as the skin, after piercing a biological barrier, such as the stratum corneum. An IRM compound, alone or in combination with another drug, including one or more vaccines, may then be applied to the pierced site, such that the IRM compound and other drug(s), if present, can pass through the pierced biological barrier. The IRM compound may be applied in any convenient manner, and the type of vehicle and duration of application will depend on the particular therapeutic outcome desired. For example, IRM compound may be applied in the form of a solution that is swabbed onto the treated target site or as a composition, such as, for example, a cream, gauze, emulsion, foam, gel, or lotion that is topically applied onto the treated site. Alternatively, an IRM compound may be applied to the surface in a form such that it remains in contact with the target site for an extended time. For example, such extended contact may be affected by applying the IRM compound in the form of a transdermal delivery patch affixed to the target site.

The IRM compound, and other drug(s), including vaccine(s), if used, may also be applied as set forth above, but prior to piercing with the microneedle device. Alternatively, the IRM compound may be applied before or after piercing with the microneedle device, and another drug delivered from the microneedle device itself (i.e., as a needle coating or from a reservoir or other deposit); or the reverse, with the IRM coated, reservoired or deposited on or in the microneedle device and another drug delivered to the site before or after piercing with the microneedle device.

Thus, it is to be understood that the methods of the present invention, include, but are not limited to, contacting a target site, such as the skin, with a microneedle device prior to, coincident with, or after the target site is contacted with one or more IRM compounds. In addition to one or more IRM compounds, the devices and methods of the present invention can include additional agents. Such additional agents may be additional drugs, including, for example, a vaccine or a tumor necrosis factor receptor (TNFR) agonist. Vaccines that may be delivered in conjunction with one or more IRM compounds and a microneedle device include any material that raises either humoral and/or cell mediated immune response, such as live or attenuated viral and bacterial immunogens and inactivated viral, tumor-derived, protozoal, organism-derived, fungal, and bacterial immunogens, toxoids, toxins, polysaccharides, proteins, glycoproteins, peptides, cellular vaccines, such as using dendritic cells, DNA vaccines, recombinant proteins, glycoproteins, and peptides, and the like, for use in connection with, e.g., BCG, cholera, plague, typhoid, hepatitis A, B, and C, influenza A and B, parainfluenza, polio, rabies, measles, mumps, rubella, yellow fever, tetanus, diphtheria, hemophilus influenza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, severe acute respiratory syndrome (SARS), anthrax, and yellow fever. Such additional agents can include, but are no limited to, drugs, such as antiviral agents or cytokines. The vaccine may be separate or may be physically or chemically linked to the IRM, such as by chemical conjugation or other means, so that they are delivered as a unit. TNFR agonists that may be delivered in conjunction with IRMs using microneedles include, but are not limited to, CD40 receptor agonists. It is also possible to deliver an IRM in conjunction with microneedle device and a vaccine, and a TNFR agonist.

The devices and methods of the present invention can be used for delivering an IRM compound and a vaccine into or across a biological barrier, including the intracutaneous delivery of an IRM compound and a vaccine. In some instances, for the delivery of an IRM compound and a vaccine as a co-coating on or from a reservoir of the microneedle device, the IRM compound is not a TLR7 agonist such as imiquimod or resiquimod (i.e., S-28463 or 4-Amino-α,α-dimethyl-1H-imidazo[4,5-c]quinoline-1-ethanol)), but is a TLR6, TLR8, and/or TLR9 agonist, and more preferably, a TLR 8 and/or TLR 9 agonist. In some instances, the intracutaneous delivery of an IRM compound and a vaccine by the devices and methods of the present invention may induce an immune response that is equal to or greater than the immune response induced by the delivery of the same or greater amount of an IRM compound and vaccine delivered by conventional subcutaneous or intramuscular injection.

The devices and methods of the present invention can be used for delivering an IRM compound across a biological barrier, including the intracutaneous delivery of an IRM compound, for the treatment of a symptom of a pathological condition. In some instances of the intracutaneous delivery of an IRM compound by the devices and methods of the present invention, a smaller effective amount of an IRM compound may be needed to treat a symptom of a pathological condition in comparison to the effective amount needed to treat the same symptom of a pathological condition with topical administration alone.

IRMs such as imiquimod—a small molecule, imidazoquinoline IRM, marketed as ALDARA (3M Pharmaceuticals, St. Paul, Minn.)—have been shown to be useful for the therapeutic treatment of warts, as well as certain cancerous or pre-cancerous lesions (See, e.g., Geisse et al., *J. Am. Acad. Dermatol.*, 47(3): 390-398 (2002); Shumack et al., *Arch. Dermatol.*, 138: 1163-1171 (2002); and WO 03/045391.

Other diseases for which IRM compounds may be used as treatments include, but are not limited to:

Viral diseases, such as genital warts, common warts, plantar warts, hepatitis B, hepatitis C, herpes simplex virus type I and type II, molluscum contagiosum, variola, HIV, CMV, VZV, rhinovirus, adenovirus, coronavirus, influenza, parainfluenza;

Bacterial diseases, such as tuberculosis, and mycobacterium avium, leprosy;

Other infectious diseases, such as fungal diseases, chlamydia, candida, aspergillus, cryptococcal meningitis, pneumocystis carnii, cryptosporidiosis, histoplasmosis, toxoplasmosis, trypanosome infection, leishmaniasis;

Neoplastic diseases, such as intraepithelial neoplasias, cervical dysplasia, actinic keratosis, basal cell carcinoma, squamous cell carcinoma, hairy cell leukemia, Karposi's sarcoma, melanoma, renal cell carcinoma, myelogeous leukemia, multiple myeloma, non-Hodgkin's lymphoma, cutaneous T-cell lymphoma, and other cancers;

TH-2 mediated, atopic, and autoimmune diseases, such as atopic dermatitis or eczema, eosinophilia, asthma, allergy, allergic rhinitis, systemic lupus erythematosis, essential thrombocythaemia, multiple sclerosis, Ommen's syndrome, discoid lupus, alopecia areata, inhibition of keloid formation and other types of scarring, and enhancing would healing, including chronic wounds; and The delivery of IRM compounds across biological barriers, including the intracutaneous delivery of IRM compounds, may be particularly helpful in individuals having compromised immune functioning, such as those with HIV AIDS, transplant patients, and cancer patients.

An amount of an IRM compound effective for a given therapeutic or prophylactic application is an amount sufficient to achieve the intended therapeutic or prophylactic application. The precise amount of IRM compound used will vary according to factors known in the art including, but not limited to, the physical and chemical nature of the IRM compound, the intended dosing regimen, the state of the subject's immune system (e.g., suppressed, compromised, stimulated), the method of administering the MM compound, and the species to which the formulation is being administered, the type of formulation being administered, the condition being treated, and any other active agents which are being co-administered with the IRM. Accordingly it is not practical to set forth generally the amount that constitutes an amount of IRM compound effective for all possible applications. Those of ordinary skill in the art, however, can readily determine the appropriate amount with due consideration of such factors.

In some embodiments, the present invention includes kits that include at least one microneedle device and at least one IRM compound. Such kits may include additional drugs, including, for example, a vaccine. Kits may also include a printed label or written instructions for the use of the microneedle device for the delivery of one or more IRM compounds across a biological barrier.

The methods, materials, and articles of the present invention may be applicable for any suitable subject. Suitable subjects include, but are not limited to, animals such as, but not limited to, humans, non-human primates, rodents, dogs, cats, horses, cows, pigs, sheep, goats, cows, birds, or fish.

The complete disclosures of the patents, patent documents and publications cited herein are incorporated by reference in their entirety as if each were individually incorporated. In case of conflict, the present specification, including definitions, shall control. Various modifications and alterations to this invention will become apparent to those skilled in the art without departing from the scope and spirit of this invention. Illustrative embodiments and examples are provided as examples only and are not intended to limit the scope of the present invention. The scope of the invention is limited only by the claims set forth as follows.

What is claimed is:

1. A method for the delivery of an immune response modifier (IRM) compound into or across a biological barrier comprising:
    contacting a biological barrier with a microneedle device comprising at least one microneedle;
    administering at least one IRM compound selected from the group consisting of amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, thioether substituted imidazoquinoline amines, and 2-propyl[1,3]thiazolo[4,5-c]quinolin-4-amine; a pharmaceutically acceptable salt thereof; and combinations thereof, into or across the biological barrier; and
    administering a vaccine;
    wherein the vaccine is a protein, glycoprotein, or peptide vaccine; and
    wherein the IRM compound is chemically linked to the vaccine and both the IRM compound and the vaccine are coated onto at least a portion of the microneedle device.

2. The method of claim 1 wherein the biological barrier is the skin and the at least one IRM compound is delivered intracutaneously.

3. The method of claim 1 wherein the IRM is a sulfonamide substituted imidazoquinoline amine selected from N-{2-[4-amino-2-(ethoxymethyl)-1H-imidazo[4,5-c]quinolin-1-yl]-1,1-dimethylethyl}methanesulfonamide, N-[4-(4-amino-2-ethyl-1H-imidazo[4,5-c]quinolin-1-yl)butyl]methanesulfonamide, and N-[4-(4-amino-2-propyl-1H-imidazo[4,5-c]quinolin-1-yl)butyl]methanesulfonamide.

4. The method of claim 1 wherein the IRM is N-{2-[4-amino-2-(ethoxymethyl)-1H-imidazo[4,5-c]quinolin-1-yl]-1,1-dimethylethyl}cyclohexanecarboxamide.

5. The method of claim 1 wherein the IRM is a urea substituted imidazoquinoline amine selected from N-{2-[4-amino-2-(ethoxymethyl)-1H-imidazo[4,5-c]quinolin-1-yl]-1,1-dimethylethyl}-N'-cyclohexylurea, and N-{2-[4-amino-2-(ethoxymethyl)-1H-imidazo[4,5-c]quinolin-1-yl]ethyl}-N'-isopropylurea.

6. The method of claim 1 wherein the at least one microneedle penetrates the biological barrier by no more than 500 μm.

7. The method of claim 1 wherein the microneedle device contacts the biological barrier for 30 seconds to 20 minutes.

8. The method of claim 1 wherein he IRM compound has a molecular weight of less than about 1000 daltons.

9. A method for the delivery of an immune response modifier (IRM) compound into or across a biological barrier comprising:
    contacting a biological barrier with a microneedle device comprising at least one microneedle;
    administering at least one IRM compound selected from the group consisting of N-{2-[4-amino-2-(ethoxymethyl)-1H-imidazo[4,5-c]quinolin-1-yl]-1,1-dimethylethyl}methanesulfonamide; N-{2-[4-amino-2-(ethoxymethyl)-1H-imidazo[4,5-c]quinolin-1-yl]-1,1-dimethylethyl}cyclohexanecarboxamide; N-{2-[4-amino-2-(ethoxymethyl)-1H-imidazo[4,5-c]quinolin-1-yl]-1,1-dimethylethyl}-N'-cyclohexylurea, and N-{2-[4-amino-2-(ethoxymethyl)-1H-imidazo[4,5-c]quinolin-1-yl]ethyl}-N'-isopropylurea; a pharmaceutically acceptable salt thereof; and combinations thereof, into or across the biological barrier; and
    administering a vaccine;
    wherein the vaccine is a protein, glycoprotein, or peptide vaccine; and
    wherein both the IRM compound and the vaccine are coated onto at least a portion of the microneedle device.

10. The method of claim 9 wherein the biological barrier is the skin and the at least one IRM compound and the vaccine are delivered intracutaneously.

11. The method of claim 9 wherein the at least one microneedle penetrates the biological barrier by no more than 500 μm.

12. The method of claim 9 wherein the microneedle device contacts the biological barrier for 30 seconds to 20 minutes.

13. The method of claim 9 wherein he IRM compound has a molecular weight of less than about 1000 daltons.

14. A method for the delivery of an immune response modifier (IRM) compound into or across a biological barrier comprising:
- contacting a biological barrier with a microneedle device comprising at least one microneedle;
- administering at least one IRM compound selected from the group consisting of urea substituted imidazoquinoline amines, sulfonamido ether substituted imidazoquinoline amines, and urea substituted imidazoquinoline ethers; a pharmaceutically acceptable salt thereof; and combinations thereof, into or across the biological barrier; and
- administering a vaccine;
- wherein the vaccine is a protein, glycoprotein, or peptide vaccine; and
- wherein the IRM compound is chemically linked to the vaccine and both the IRM compound and the vaccine are coated onto at least a portion of the microneedle device.

15. The method of claim 14 wherein the biological barrier is the skin and the at least one IRM compound is delivered intracutaneously.

16. The method of claim 14 wherein the IRM is a urea substituted imidazoquinoline amine selected from N-{2-[4-amino-2-(ethoxymethyl)-1H-imidazo[4,5-c]quinolin-1-yl]-1,1-dimethylethyl}-N'-cyclohexylurea, and N-{2-[4-amino-2-(ethoxymethyl)-1H-imidazo[4,5-c]quinolin-1-yl]ethyl}-N'-isopropylurea.

17. The method of claim 14 wherein the at least one microneedle penetrates the biological barrier by no more than 500 μm.

18. The method of claim 14 wherein the microneedle device contacts the biological barrier for 30 seconds to 20 minutes.

19. The method of claim 14 wherein he IRM compound has a molecular weight of less than about 1000 daltons.

* * * * *

UNITED STATES PATENT AND TRADEMARK OFFICE
CERTIFICATE OF CORRECTION

PATENT NO. : 8,961,477 B2
APPLICATION NO. : 10/595073
DATED : February 24, 2015
INVENTOR(S) : James Wolter Page 1 of 2

It is certified that error appears in the above-identified patent and that said Letters Patent is hereby corrected as shown below:

Title page (Other Publications)
Line 4          Delete "Immnology," and insert -- Immunology --, therefor.

Page 3, (Other Publications)
Line 8          Delete "Mefthod.",") and insert -- Method." --, therefor.

Specification

Column 6
Line 3          Delete "DIM" and insert -- IRM --, therefor.
Line 22         Delete "laproscopic" and insert -- laparoscopic --, therefor.

Column 7
Line 41         Delete "the a" and insert -- the --, therefor.

Column 8
Line 19         Delete "thermoplastice" and insert -- thermoplastic --, therefor.
Line 31         Delete "MM" and insert -- IRM --, therefor.

Column 9
Line 18         Delete "that" and insert -- than --, therefor.

Column 12
Line 44         Delete "M" and insert -- IRM --, therefor.

Signed and Sealed this
Thirty-first Day of May, 2016

Michelle K. Lee
*Director of the United States Patent and Trademark Office*

CERTIFICATE OF CORRECTION (continued)
U.S. Pat. No. 8,961,477 B2

<u>Column 13</u>
Line 60                 Delete "hemophilus" and insert -- haemophilus --, therefor.
Line 66                 Delete "no" and insert -- not --, therefor.

<u>Column 14</u>
Line 59                 Delete "Karposi's" and insert -- Kaposi's --, therefor.
Line 60                 Delete "myelogeous" and insert -- myelogenous --, therefor.
Line 65                 Delete "erythematosis," and insert -- erythematosus, --, therefor.
Line 66                 Delete "thrombocythaemia," and insert -- thrombocythemia, --, therefor.
Line 66                 Delete "Ommen's" and insert -- Omenn's --, therefor.

<u>Column 15</u>
Line 17 (Approx.)     Delete "MM" and insert -- IRM --, therefor.